United States Patent [19]

Sih

[11] 3,962,352
[45] June 8, 1976

[54] 3-SUBSTITUTED IODO ALKENYL COMPOUNDS AND METHODS FOR PREPARING SAME

[75] Inventor: Charles J. Sih, Madison, Wis.

[73] Assignee: Wisconsin Alumni Research Foundation, Madison, Wis.

[22] Filed: Sept. 9, 1974

[21] Appl. No.: 504,162

Related U.S. Application Data

[60] Division of Ser. No. 293,442, Sept. 29, 1972, abandoned, which is a continuation-in-part of Ser. No. 255,728, May 22, 1972, abandoned.

[52] U.S. Cl............................ 260/633; 260/345.9; 260/617 C; 260/618 H; 260/468 D
[51] Int. Cl.².......................................... C07C 33/10
[58] Field of Search......... 260/345.9, 617 C, 618 H, 260/633

[56] References Cited
OTHER PUBLICATIONS

Sih et al., J. Am. Chem. Soc., 97, 857 (1975).
Sih et al., Tetrahedron Letters, 24, 2435 (1972).
McOmie, Advances in Org. Chem., vol. 3, pp. 218–219 (1963).
Zweifel et al., J. Am. Chem. Soc., 89, 2753 (1967).
Sih et al., J. Am. Chem. Soc., 94, 3643 (1972).

*Primary Examiner*—James O. Thomas, Jr.
*Assistant Examiner*—Nicky Chan
*Attorney, Agent, or Firm*—Howard W. Bremer

[57] ABSTRACT

Compounds of the formula:

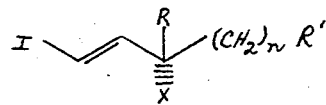

where
R is hydrogen, methyl or ethyl;
R' is hydrogen, a saturated hydrocarbon chain containing from 1 to about 9 carbon atoms, pentene, hexene, cyclohexyl, or benzyl
X is hydrogen, pyranoxy, OR'' where R'' is a hydrocarbon chain containing from 1 to about 5 carbon atoms or benzyl,

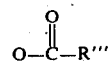

where R''' is a hydrocarbon chain containing from 1 to about 8 carbon atoms or benzyl, or

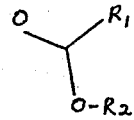

where $R_1$ and $R_2$ are each a hydrocarbon chain containing from 1 to about 5 carbon atoms, and
n is an integer from 0 to 5

These compounds are key intermediates in the production of prostaglandins and exhibit antibacterial properties.

4 Claims, No Drawings

3-SUBSTITUTED IODO ALKENYL COMPOUNDS AND METHODS FOR PREPARING SAME

CROSS-REFERENCE TO OTHER APPLICATION

This application is a division of application Ser. No. 293,442, filed Sept. 29, 1972, now abandoned, which is a continuation-in-part of application Ser. No. 255,728, filed May 22, 1972 now abandoned, and entitled "3-Substituted Iodo Alkenyl Compounds and Methods for Preparing Same."

The invention described herein was made in the course of work under a grant or award from the Department of Health, Education, and Welfare.

This invention relates to compounds which are eminently useful as intermediates in the preparation of prostaglandins and to methods for preparing such compounds.

The prostaglandins are currently of great interest because of the broad physiologic responses which they elicit in animals, including man. Development of potential application of these compounds has been limited however because of their general unavailability. If they are prepared by total chemical synthesis the processes are long and tedious and the yields of product are low. If they are derived from natural sources difficulties are experienced because of the limitation on the surface material from which they are extracted and in obtaining them in significant amounts and inconsistences are encountered in the activities of the compounds extracted on different occasions.

Process for substantially improving the available supply of prostaglandins, as well as new compounds which can function as intermediates in the preparation of known prostaglandins or compounds having prostaglandin-like activity are described in co-pending application Ser. No. 221,058, filed Jan. 26, 1972.

It is the primary purpose of this invention to provide new compounds which find application as key intermediates in the processes of the above-referenced patent application, as well as in other processes, directed to the preparation of known prostaglandins or compounds having prostaglandin-like or anti-prostaglandin-like activity and to methods for preparing such intermediates. The compounds of this invention also exhibit anti-bacterial activity against gram positive bacteria.

The compounds of this invention have the general formula:

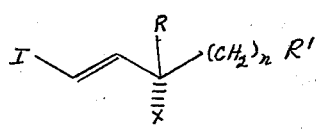

where
R is hydrogen, methyl or ethyl;
R' is hydrogen, a saturated hydrocarbon chain containing from 1 to 9 carbon atoms, pentene, hexene, cyclohexyl, or benzyl
X is hydrogen, pyranoxy, OR" where R" a hydrocarbon chain containing from 1 to about 5 carbon atoms or benzyl,

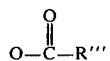

where R''' is a hydrocarbon chain containing from 1 to about 8 carbon atoms or benzyl, or

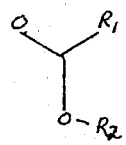

where $R_1$ and $R_2$ are each a hydrocarbon chain containing from 1 to about 5 carbon atoms, and
$n$ is an integer from 0 to 5.

Among such compounds are included:
3-hydroxy-1-iodo-1-trans-octene
3-hydroxy-1-iodo-1-trans-pentene
3-hydroxy-1-iodo-1-trans-hexene
3-hydroxy-1-iodo-1-trans-4-methyl heptene
3-hydroxy-1-iodo-1-trans-4-ethyl hexene 3-hydroxy-3-methyl-1-iodo-1-trans-octene
3-hydroxy-3-ethyl-1-iodo-1-trans-octene
3-pyranoxy-1-iodo-1-trans-octene
3-(α-ethoxy)-ethoxy-1-iodo-1-trans-octene
3-benzyloxy-1-iodo-1-trans-octene
3-acetyloxy-1-iodo-1-trans-octene
3-hydroxy-1-iodo-1-trans-heptene
3-hydroxy-1-iodo-1-trans-1,6-octadiene
3-hydroxy-1-iodo-1-trans-1,6-nonadiene
3-hydroxy-1-iodo-4-cyclohexyl-1-trans-butene
3-hydroxy-1-iodo-5-cyclohexyl-1-trans-pentene
3-hydroxy-1-iodo-6-cyclohexyl-1-trans-hexene
3-hydroxy-1-iodo-7-cyclohexyl-1-trans-heptene
3-hydroxy-1-iodo-8-cyclohexyl-1-trans-octene
3-hydroxy-1-iodo-4-benzyl-1-trans-butene
3-hydroxy-1-iodo-5-benzyl-1-trans-pentene
3-hydroxy-1-iodo-6-benzyl-1-trans-hexene
3-hydroxy-1-iodo-7-benzyl-1-trans-heptene
3-hydroxy-1-iodo-8-benzyl-1-trans-octene
1-iodo-4-cyclohexyl-1-trans-butene
1-iodo-5-cyclohexyl-1-trans-pentene
1-iodo-6-cyclohexyl-1-trans-hexene
1-iodo-7-cyclohexyl-1-trans-heptene
1-iodo-8-cyclohexyl-1-trans-octene
1-iodo-4-benzyl-1-trans-butene
1-iodo-5-benzyl-1-trans-pentene
1-iodo-6-benzyl-1-trans-hexene
1-iodo-7-benzyl-1-trans-heptene
1-iodo-8-benzyl-1-trans-octane These compounds can be prepared in accordance with the procedure set forth in the following example which, by way of illustrating the process, relates specifically to the preparation of 3-hydroxy-1-iodo-1-trans-octene.

EXAMPLE 1

2 molar equivalents of diisobutylaluminum hydride was added to 1 molar equivalent of 1-octyn-3-ol in dry heptane (40 ml/100 m moles of 1-octyn-3-ol) while maintaining the temperature below 40° C. When the exothermic reaction and subsided, the reaction mixture was heated at about 50° C. for 2.5 hours. The heptane was then removed under reduced pressure (0.2 mm Hg) and the residue obtained was diluted with dry tetrahydrofuran (40 ml/100 m moles of diisobutylaluminum hydride). To this solution, cooled to −50° C., was slowly added a solution of 2 molar equivalents of iodine in dry tetrahydrofuran (40 ml/100 m moles of iodine) while maintaining the temperature at about −50° C. The iodine colour disappeared at the beginning and a gas (probably hydrogen) was given off. After about 1 molar equivalent of iodine was added, the gas evolution ceased and the iodine colour disappeared more slowly, the solution taking on a red colour. After all the iodine has been added, the reaction mixture was allowed to warm up to room temperature, whereupon the diisobutylalane formed in the reaction was decomposed at 20°–30° C. by the dropwise addition of 20% sulfuric acid. When the isobutane evolution had diminished, the reaction mixture was poured into ice –20% sulfuric acid. The reaction mixture was extracted four times with pentane and the combined organic extract was washed successively with sodium thiosulfate, saturated sodium bicarbonate and saturated sodium chloride solutions, and dried over magnesium sulfate. Evaporation of the dried extract gave a yellow oil. The nmr spectrum (CDCl₃) of the product after all volatile material had been distilled off, showed that some of the saturated iodide, 3-hydroxy-1-iodooctane was present.

The product was further treated to remove any 3-hydroxy-1-iodo-octane and possible diiodo-3-hydroxyoctane present. To accomplish this the reaction product was mixed with an excess (3–5 times) of triethylamine and the mixture heated at about 94° C. for 20 hours. The excess triethylamine was evaporated off and water was added to the residue. The mixture was shaken for some time. Most of the black oily residue dissolved in the water and the total mixture was extracted five times with pentane. The combined pentane extract was washed successively with dilute hydrochloric acid, saturated sodium bicarbonate, sodium thiosulfate, saturated sodium bicarbonate and saturated sodium chloride solutions and dried over magnesium sulfate. The product obtained after evaporation of the pentane was chromatographed on silica gel and elution with benzene produced pure 3-hydroxy-1-iodo-1-trans-octene, wt: 12.5 g. (24.6%).

As an alternative to the procedure of Example 1 above, the hydroalumination can be carried out by complexing the hydroxy function in 1-octyn-3-ol with trisobutylaluminum to give an aluminum alkoxide and isobutane gas, one molar equivalent of diisobutylaluminum hydride then being added to form the vinylalane. This procedure, which is set out with greater specificity in Example 2 below, offers certain advantages over the procedure of Example 1, above, in that the quantity of undersired 1-iodo-3-hydroxyoctane and diiodo-3-hydroxyoctane formed in the reaction mixture is reduced and the desired product, 3-hydroxy-1-iodo-1-trans-octene, can be obtained in higher yields by vacuum distillation.

EXAMPLE 2

To 1.26 g. (0.01 moles) of 1-octyn-3-ol in 8 ml. in dry heptane was added dropwise 6.18 ml. (0.03 moles) of triisobutylaluminum at 10°–15°C.; 1.82 ml. (0.01 moles) of diisobutylaluminum hydride was then added and the reaction mixture was heated at 50°14 55° C. for 2 hours. The solution was then cooled and the heptane removed under reduced pressure. The residue obtained was diluted with 12 ml. of dry tetrahydrofuran. After cooling the solution to –50° C., 10.26 g. (0.04 moles) of iodine in 16 ml. of dry tetrahydrofuran was added dropwise. The dark solution was warmed to room temperature and the alane was decomposed at 20°–30° C. with 20% H₂SO₄. After the isobutane evolution had diminished, the reaction mixture was poured into ice and extracted four times with pentane. The pentane extract was washed successively with saturated NaHCO₃, sodium thiosulfate, saturated NaHCO₃ and saturated NaCl solutions. After drying the pentane over MgSO₄, it was evaporated to given a dark oil. To remove the iodo-3-hydroxyoctane, the mixture was heated for 16 hours at 90° C. with 0.005 moles of triethylamine. The excess triethylamine was evaporated off and water was added to the residue. Most of the dark oily residue dissolved in the aqueous layer and the total mixture was extracted with pentane. The pentane extract was washed with dilute hydrochloric acid, saturated sodium bicarbonate and saturated sodium chloride solutions and dried over magnesium sulfate. After evaporation of the pentane, the residue was distilled in vacuo to yield pure 3-hydroxy-1-iodo-1-trans-octene (40–50% molar basis). Some 1-octyn-3-ol was recovered.

The hydroalumination methods of the foregoing Examples are readily applicable to compounds having the formula

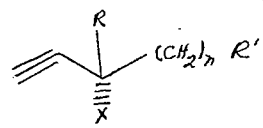

where
R is hydrogeh, methyl or ethyl;
R′ is hydrogen, a saturated hydrocarbon chain containing from 1 to about 9 carbon atoms, pentene, hexene, cyclohexyl, or benzyl
X is hydrogen, pyranoxy, OR″ where R″ is a hydrocarbon chain containing from 1 to about 5 carbon atoms or benzyl,

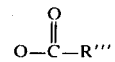

where R′′′ is a hydrocarbon chain containing from 1 to about 8 carbon atoms or benxyl, or

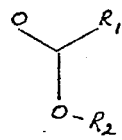

where $R_1$ and $R_2$ are each a hydrocarbon chain containing from 1 to about 5 carbon atoms, and
n is an integer from 0 to 5
to produce the iodo compounds hereinbefore set forth.

Of the compounds which respond to the above formula 1-octyn-3-ol is a preferred rectant. Other of the compounds responding to the said formula which find ready application include those in which X is an ether configuration which is susceptible to hydrolysis by mild acid, including cyclic ether, or where X is an ester configuration (for example 3-acyloxy-1-octyne compounds such as 3-acetoxy-1-octyne).

The aluminum complexing agent in each case will be chosen to provide the greatest possible yield of desired product. For example, it has been found that when 3-tetra-pyranoxy-1-octyne, 3-(αethoxy)-ethoxy-octyne or 3-acetoxy-1-octyne are the compounds of choice for hydroalumination, the process described in Example 1 provides a better yield of the desired compound, 3-hydroxy-1-iodo-1-trans-octene, than does the procedure of Example 2. However, as is pointed out more specifically below, when diisobutylaluminum is used as the hydroalumination agent, it is essential to use that agent in the ratio of two molar equivalents to one molar equivalent of the particular compound which is being complexed. On the other hand, when triisobutylaluminum is used, as in the process of Example 2, such agent can be used in a molar equivalent ratio to the compound being complexed of 1:1 or greater.

It is also to be understood that the saturated hydrocarbon chain represented by R' in the foregoing general formulae does not have to be a straight chain configuration but can be branched. For example, 4-, 5-, or 6-, methyl heptyne or other branched chain configurations can be readily substituted for the hydrocarbon chain in the 1-octyn-3-ol reactant.

The hydroalumination process as described in Example 1 above, and where diisobutylaluminum is used as the hydroalumination agent, is similar to the general procedure described by G. Zweifel et al, J. Amer. Chem. Soc. 89, 2753 (1967). There are, however, some major, and critical, differences. With the 3-position substituted, compounds which must be used as the starting materials to produce the novel compounds of this invention, the Zweifel et al process is inoperative. It is only when two molar equivalents of the hydroalumination agent, diisobutylaluminum hydride, are used that the hydroalumination proceeds to produce the desired compounds. In addition, the treatment with triethylamine or, other basic trialkylamines, such as, for example, trimethylamine is essential to the elimination of undesirable by-products from the reaction mixture and to the production of the desired compound in essentially pure form.

The processes of this invention permit the ready recovery of the products thereof in the trans isomeric configuration, the preferable isomer for the preparation of physiologically-active prostaglandins or compounds having prostaglandin-like activity.

The iodo compounds of this invention are readily converted into the corresponding lithium compounds in accordance with the procedure described in the following Example which is directed, by way of illustration, to the preparation of 1-lithium-1-trans-octene.

EXAMPLE 3

In a three-necked round bottom flask equipped with a mechanical stirrer (wire blade) and pressure equalizing dropping funnel was placed 4–6 molar equivalents of fine lithium powder and dry diethyl ether (2 ml/1 mmole of vinyl iodide) freshyl distilled over lithium aluminum hydride. A blanket of argon was maintained at all times. To this rapidly stirred mixture, which was cooled in an ice-bath, was added 1 molar equivalent of 3-hydroxy 1-iodo-1-trans-octene (vinyl iodide) in dry diethylether (2 ml/1 mmole of vinyl iodide). After a few drops of the vinyl iodide in ether was added, a Gilman test was performed. If the test was positive, the addition of the vinyl iodide was continued. If the test was negative, the addition of the vinyl iodide was stopped and the rapid stirring of the lithium solution continued. The Gilman test was performed at various intervals. When a positive test was obtained, the addition of the vinyl iodide was recommenced. The vinyl iodide solution was added over 2 hours. The solution was stirred with ice-bath bath cooling for a further 4 hours. The solution of the vinyl lithium was transferred to a storage bottle under argon through a glass wool filter to filter out any unreacted lithium.

The 1-lithium-1-trans-octene was utilized in preparing prostaglandins in accordance wit the procedures shown in the aforementioned co-pending application and the following Example.

EXAMPLE 4

A solution of tri-n-butylphosphine-copper (I) iodide complex (1.6127 g.) in 21 ml. of dry diethyl ether was treated with 34 ml. of 0.242 M solution of 1-lithium-1-trans-octene in either at −78° C. under a blanket of nitrogen. After stirring at −78° C. for 30 minutes, 1.33 g. of 2-(6′carboethyoxyhexyl)-2-cyclopentene-4-tetrahydropyranoxy-1-one (method of preparation shown in "Total Synthesis of (+)-15-Deoxyprostaglandin $E_1$", Charles J. Sih et al, Chem. Comm. No. 4, p. 240 (1972)) in 25 ml. of dry diethyl ether was added dropwise to the yellow vinyl copper solution. The solution was allowed to warm to 0° C. (ice-bath) and stirred at this temperature for 1.5–2 hours. The reaction mixture was allowed to warm to room temperature and 28 ml. of a 20% aqueous ammonium chloride solution, pH 8.3, was added to complex the copper. The ethereal layer was separated from the blue aqueous layer, which was extracted three times with ether. The combined ether extracts were washed twice with a saturate sodium chloride solution and dried over magnesium sulfate. Evaporation of the ethereal extract afforded a reddish yellow oil. This oil was dissolved in 10 ml. of acetic acid-water (65:35) and tetrahydrofuran in the ratio of 1 to 0.1 ml. and was stirred at 30° C. overnight according to the procedure of E. J. Corey, T. K. Schaaf, W. Huber, U. Koelliber and N. Weinshenker, J. Amer. Chem. Soc., 92, 397 (1970). The solvent was removed and the oil product was chromatographed over a silicic acid-Celite (85:15) column (¾× 4 inches ). The column was eluted with a gradient system consisting of 400 ml. of benzene-ethyl acetate (75:25) in the reservoir. 7 ml. fractions were collected. Fractions 33–48 afforded 155 mg. of ultraviolet positive material which had the following characteristics: nmr $(COCl_3)\delta1.21$ (t, 3, J = HZ, $CH_3$), δ3.23(m, 1, H at C-12), δ4.13 (q 2, J = 6,7 HZ, $CH_3CH_2$), δ5.62 (m, 2, vinyl H at C-13 and C-14), δ 6.17 (m, 1, H at C-10), δ 7.49 (m, 1, H at c-11); m/e at 348; $\lambda max^{alc}$ 217 nm (10,000) and was identified thereby as dl 15 deoxo $PGA_1$ ethyl ester.

Fractions 65–100 were pooled and evaporated to dryness to yield 717 mg. of a material having the following characteristics: nmr $(CCl_4, 100 m HZ)\delta1.21$ (t, 3, J = 6.7 HZ, $CH_3$), δ4.13 (q, 2, J =6.7 HZ, $CH_3CH_2$), δ4.20 (m, 1, H—C—OH), δ5.28 (d of d, $J_{12,13} = 7$ HZ, $J_{13,14} = 16$ HZ - $C_{13} \approx$), 5.58 (d of t, $J_{13,14}$ - 16 HZ, $J_{14,15}= 6$ HZ, ≈ $C_{14}$H-); ir (Nujol) 962 $cm^{-1}$ (trans CH=CH); molecular ion a m/e 366.28145 (theory for $C_{22}H_{38}O_4$, 366.27699) and which was determined to be dl-15-deoxoprostaglandin $E_1$ ethyl ester.

This ester can be readily to dl-15-deoxo $PGE_1$ by methods which are well known in the art, such as, for example, by exposing it to the action of an esterase-producing microorganism. (Sih et al, Chem. Comm. supra.)

Pharmacological assays were conducted with dl-15-deoxo-prostaglandin $E_1$ using the guinea pig tracheal strip (smooth muscle) methods described by J. W. Constantine, Journal Pharmacy & Pharmacolog 17, 3184 (1955) and R. Patterson, Journ. Allergy 29, 165

(1958). dl-15-deoxoprostaglandin $E_1$ exhibited an $ED_{50}$ concentration (effective dose giving 50% of maximum response) on separate determinations of $1.4 \times 10^{-6}$ M and $1.06^{-6}$M indicating its pharmacological applicability in place of natural prostaglandins where smooth muscle controlling or responsive effects are being sought.

In addition to having utility as key intermediates in the total chemical synthesis of prostaglandins as described hereinbefore and in co-pending application Ser. No. 221,058, filed Jan. 26, 1972, the compounds of this invention are characterized by activity against gram positive bacteria as is shown in Example 5 below.

EXAMPLE 5

To ten ml. of Penicillin assay seed agar (J-1095-C, Fisher Scientific Co.) per petri-dish was added 0.1 ml. of a 24 hour culture of the test organisms in nutrient broth. The test compounds 3-hydroxy-1-iodo-1-trans-octene (HVI) and 1-iodo-1-trans-octene (VI) was dissolved in method to give a concentration of $1.9 \times 10^{-2}$ M. One-tenth milliter of the test compounds was added to a filter paper disk (12.7 mm.), which was layered on top of the agar plate. The petri-plate was incubated at 25° C. for 48 hours, and the zone of inhibition was measured.

| Test Organisms | Zone diameter (mm) | |
| --- | --- | --- |
|  | VI | HVI |
| *Bacillus Subtilis* | — | 23 |
| *Sarcina lutea* | — | 22 |
| *Escherichia Coli* | — | — |
| *Staphylococcus aureus* | — | — |

It is evident from the above that the 3-carbon-substituted compounds of this invention exhibit substantial antibacterial activity against gram positive organisms as compared with smilar compounds not having a substituent at that position in the hydrocarbon chain.

Having thus described the invention what is claimed is:

I claim:

1. A method for preparing compounds having the formula

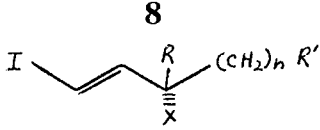

where
R is hydrogen, methyl or ethyl
R' is hydrogen, a saturated hydrocarbon chain containing from 1 to about 9 carbon atoms, pentene, hexene, cyclohexyl or benzyl,
and *n* is an integer from 0 to 5
which comprises reacting one molar equivalent of a compound having the formula where R, R', X and *n* have the designations set forth above,
with at least one molar equivalent of triisobutylaluminum,
reacting the resulting alkoxide with diisobutylaluminum hydride,
iodinating the resulting hydroalumination product,
treating the resulting mixture with sulfuric acid to decompose the alane formed
treating the resulting mixture with an excess of a basic trialkyl amine,
and recovering the desired product from the reaction mixture.

2. The process of claim 1 wherein the basic trialkyl amine is triethylamine.

3. The process of claim 1 wherein the basic trialkyl amine is trimethylamine.

4. The method for preparing 3-hydroxy-1-iodo-1-trans octene which comprises reacting at least one molar equivalent of triisobutylaluminum hydride with one molar equivalent of 1-octyn-3-ol, reacting the resulting alkoxide with diisobutylaluminum hydride, iodinating the resulting hydroalumination product, treating the resulting mixture with sulfuric acid to decompose the alane formed, treating the iodination mixture with an excess of triethylamine and recovering the 3-hydroxy-1-iodo-1-trans octene from the resulting mixture.

* * * * *

UNITED STATES PATENT OFFICE
CERTIFICATE OF CORRECTION

Patent No. 3,962,352        Dated June 8, 1976

Inventor(s) Charles J. Sih

It is certified that error appears in the above-identified patent and that said Letters Patent are hereby corrected as shown below:

Column 3, line 59, "50° 14 55°" should read --50-55°--; Column 4, line 30, "hydrogeh" should read --hydrogen--; Column 6, line 57, "$C_{22}H_{38}O_4$" should read --$C_{22}H_{38}O_4$--.

Column 8, after the definition of R' and before the definition of n insert --X is hydroxyl--.

Signed and Sealed this

Fourteenth Day of September 1976

[SEAL]

Attest:

RUTH C. MASON
*Attesting Officer*

C. MARSHALL DANN
*Commissioner of Patents and Trademarks*